United States Patent
Maier

(10) Patent No.: US 7,925,324 B2
(45) Date of Patent: Apr. 12, 2011

(54) MEASURING THE FEMORAL ANTETORSION ANGLE γ OF A HUMAN FEMUR IN PARTICULAR ON THE BASIS OF FLUOROSCOPIC IMAGES

(75) Inventor: Christian Maier, Munich (DE)

(73) Assignee: Brainlab AG, Feldkirchen (DE)

( * ) Notice: Subject to any disclaimer, the term of this patent is extended or adjusted under 35 U.S.C. 154(b) by 1177 days.

(21) Appl. No.: 11/560,372

(22) Filed: Nov. 16, 2006

(65) Prior Publication Data

US 2007/0161929 A1      Jul. 12, 2007

Related U.S. Application Data

(60) Provisional application No. 60/754,511, filed on Dec. 28, 2005.

(51) Int. Cl.
*A61B 5/00* (2006.01)
(52) U.S. Cl. ........ 600/407; 600/425; 600/429; 702/150; 702/151; 702/152; 702/153; 382/128; 382/286
(58) Field of Classification Search .................. 600/407, 600/424, 425, 429; 702/150–153; 382/128, 382/286, 289
See application file for complete search history.

(56) References Cited

U.S. PATENT DOCUMENTS 5,728,128 A    3/1998  Crickenberger et al.
2005/0015003 A1*  1/2005  Lachner et al. ............... 600/424

OTHER PUBLICATIONS

K.L. Hermann, et al., "Measuring Anteversion in the Femoral Neck from Routine Radiographs", ACTA RADIOL, vol. 39, No. 4, Jul. 1998, pp. 410-415.
R. Hoffstetter et al., "Computer-Assisted Fluoroscopy-Based Reduction of Femoral Fractures and Antetorsion Correction", Computer Aided Surgery, vol. 5, 2000, pp. 311-325.
Stephen B. Murphy et al., "Femoral Anteversion", The Journal of Bone and Joint Surgery, Incorporated, vol. 69, No. 8, Oct. 1987, pp. 1169-1176.

* cited by examiner

*Primary Examiner* — Brian Casler
*Assistant Examiner* — Christopher Cook
(74) *Attorney, Agent, or Firm* — Renner, Otto, Beisselle & Sklar, LLP

(57) ABSTRACT

A method for defining an antetorsion angle γ of a femur is provided. The antetorsion angle γ is defined by two angles α' and β that can be determined by means of two images of the femur, wherein the equation tan γ=tan α'/(cos β·cos θ) can be used to calculate the antetorsion angle γ.

16 Claims, 4 Drawing Sheets

MEASURING THE FEMORAL ANTETORSION ANGLE γ OF A HUMAN FEMUR IN PARTICULAR ON THE BASIS OF FLUOROSCOPIC IMAGES

RELATED APPLICATION DATA

This application claims priority of U.S. Provisional Application No. 60/754,511 filed on Dec. 28, 2005, which is incorporated herein by reference in its entirety.

FIELD OF THE INVENTION

The present invention relates to a system and method for determining an antetorsion angle γ of a femur, such as a human femur.

BACKGROUND OF THE INVENTION

In certain medical procedures, there is a need to determine or measure the antetorsion angle of the human femur. Known methods for measuring the antetorsion angle of the human femur use different means, such as, for example, pre-operative X-ray images, CT data or intra-operative fluoroscopic images. Prior art references referring to such methods include: Egund, N., Palmer, J. "Femoral anatomy described in cylindrical coordinates using computed tomography", Acta Radiol. Diagn 1984; 25:209-215; Herman, K L, Egund, N.: "Measuring anteversion in the femoral neck from routine radiographs", Acta Radiol; 1998; 39:410-415; Herman, K. L., Egund, N: "CT measurement of anteversion in the femoral neck: the influence of femur positioning", Acta Radiol 1997; 38:527-532; Murphy, S., Simon, S., Kijewski, P., et al. "Femoral anteversion". Journal of Bone Joint Surgen 1987; 69A:1169-1176; Sugano, N., Noble, P., Kamaric E. "A comparison of alternative methods of measuring femoral anteversion", Journal Computer Assisted Tomography 1998; 22(4): 610-614; Hofstetter, R., Slomoczykowski, M., Krettek, C., et al.: "Computer-assisted fluoroscopy-based reduction of femoral fractures and antetorsion correction", Computer Aided Surgery 2000; 5(5):311-325.

Another approach in the prior art relates to a measurement device which is inserted into an intramedullary canal of a human femur and, thus, involves major surgery. This measurement device is described in U.S. Pat. No. 5,728,128.

The above prior art methods for determining or measuring the antetorsion angle of the human femur seriously impact the body of a patient, either by means of high X-ray doses, a surgical operation and/or the like.

SUMMARY OF THE INVENTION

The present invention provides a system and method for measuring or determining an antetorsion angle γ of a femur, such as a human femur. The system and method provide a simple means for measuring the antetorsion angle γ, wherein the measurement does not impact the human being or animal. The system and method allow the use of low X-ray doses while providing accurate and reliable data for determining the angle in question.

For a human, the antetorsion angle γ is defined by an angle between a central axis through the femoral neck of the femur and a posterior condyle axis.

The central axis running through the center of the femoral neck is parallel to a cortical surface of a proximal part of the femoral neck. The posterior condyle axis connects the most posterior points of the femoral condyles of the femur if the central axis through the femoral neck and the posterior condyle axis are projected onto a plane normal to the femoral shaft axis, wherein the femoral shaft axis is the central axis of the approximately cylindrically shaped shaft of the human femur. The central axis of the cylindrical shaft is parallel to the most anterior tangent to the distal femur, and the femoral shaft axis also being perpendicular to the posterior condyle axis.

A method for determining the antetorsion angle γ includes: taking a first image of the posterior condyle of the femur, such that the two posterior condyles overlap laterally, such that the posterior condyle axis can be projected onto a point, and the normal to the image plane is parallel to the posterior condyle axis; defining the most anterior tangent to the anterior cortex of the distal femur; shifting said tangent parallel to itself until it includes the point of the posterior condyle axis, thus determining the transcondylar plane; determining a parallel to the femoral shaft axis; taking a second image of the femoral neck of the femur such that the normal to the image plane of the second image encloses an angle β with the femoral shaft axis and an angle θ with the transcondylar plane; defining the femoral neck axis enclosing the angle α' with the transcondylar plane; and calculating the antetorsion angle γ by means of the equation tan γ=tan α'/(cos β·cos θ).

Another method for determining the antetorsion angle γ includes: taking a first image of the posterior condyles of the femur, such that the posterior arcs of the condyles overlap laterally, such that the posterior axis can be projected onto a point, and the normal to the image plane is parallel to the posterior condyle axis; defining the most anterior tangent to the anterior cortex of the distal femur; shifting said tangent parallel to itself until it includes the point of the posterior condyle axis, thus determining the transcondylar plane; determining a parallel to the femoral shaft axis.

After the first image has been obtained and its intended orientation with respect to the transcondylar plane of the femur has been reached, it is possible that the second image cannot be obtained in an optimal relationship to the transcondylar plane. In other words, it is possible that there is a tilt angle of the second image with respect to the normal of the transcondylar plane. This tilt angle θ can be determined on the basis of data with respect to an orientation of the camera used to obtain the second image.

In an optimized case, this tilt angle θ should be zero or close to zero. However, if the tilt angle θ is present and not negligible, an attempt should be made to avoid obtaining more than two images. This avoids placing an additional burden on the patient. Therefore, the tilt angle θ should be determined, after which the femoral neck axis enclosing the angle α (when θ=0, α=α') with the transcondylar plane can be defined, and the antetorsion angle γ can be calculated by means of the formula tan γ=tan α'/cos β.

If it is possible to avoid tilting the second image by the angle θ, then it is possible to obtain the second image of the femoral neck of the femur from a lateral direction, such that the normal to the image plane of the second image encloses an angle β with the femoral shaft axis, but not the angle θ.

As set forth above, the angle θ can be determined in the following equation: tan γ=tan α'/(cos β·cos θ). If there is no tilt of the second image with respect to the normal of the transcondylar plane, i.e., cos θ=1, the equation reads as follows: tan γ=tan α'/cos β. The latter equation can be used if the second image is taken from a truly lateral direction.

The central axis through the femoral neck runs through the center of the femoral head and always has the same distance from the cortical surface of the proximal part of the femoral neck. The central axis should be parallel to the cortical surface.

Using the method, a truly lateral image of the posterior condyles can be achieved, wherein the truly lateral image is given when both of the condyles overlap in the lateral fluoroscopic image acquired as the first image. In a truly lateral image, a posterior condyle axis is projected onto a single point and the normal to the image plane is parallel to the posterior condyle axis. This single point on the fluoroscopic image, i.e., in the plane of the fluoroscopic image, defines the posterior condyle axis in the three-dimensional space in which the femur is to be studied and localized. By means of the same lateral image (e.g., the first image in terms of the method described herein) of the posterior condyles, the most anterior tangent to the anterior cortex of the distal femur can be defined. Since the fluoroscopic image is two-dimensional, the tangent line corresponds to the transcondylar plane, which can be acquired by shifting the tangent line parallel to the posterior direction until it includes the posterior condyle axis.

The transcondylar plane achieved in this way is intersected by a plane normal to the posterior condyle axis in order determine the parallel to the femoral shaft axis. In the direction of the femoral shaft axis is the normal of the projection plane onto which the femoral neck axis and the posterior condyle axis are projected. The second or axial image of the femoral neck then can be obtained. The axial image is a common projection which is preferably used by trauma surgeons. As can be seen, other directions also may be used, wherein the second image may be obtained from a lateral direction. A navigation system such as Vector Vision/Trauma 2.5, both products of the assignee of the present application, can be used to indicate whether the imaging direction is parallel to the transcondylar plane. It is preferable to use the navigation system such that the correct imaging direction can be indicated before the second or axial image is obtained. The normal to the image plane of the axial image encloses the angle $\beta$ with the femoral shaft axis, the orientation of which corresponds in a preferred case to the Y-axis in the three-dimensional coordinate system, which is also preferred. The surgeon can define the femoral neck axis on the basis of the second image. The femoral neck axis encloses the angle $\alpha$ with the transcondylar plane. Lastly, by means of the angles $\alpha$ and $\beta$, it is possible to calculate the antetorsion angle $\gamma$ using the above-mentioned equation $\tan \gamma = \tan \alpha'/\cos \beta$.

The method is advantageous in that the antetorsion angle can be acquired by direct measurement with a high degree of accuracy. Only two fluoroscopic images are obtained, such that the radiation exposure for the patient can be dramatically reduced. In addition, it is not necessary to perform invasive surgery into the body of a patient. On the other hand, accuracy can be further improved by fixing a reference array or marker array to the femoral bone. However, it is also possible to fix the reference or marker array to an operation table on which the patient and thus the femur of the patient is located.

At least one of the first and second images can be a fluoroscopic image. At least one of the steps performed before the second image is taken can be performed on the basis of the first image. Furthermore, it is preferable to acquire the parallel by intersecting the transcondylar plane with a plane normal to the posterior condyle axis as already indicated above.

The second image can be an axial image of the femoral neck, in order to correspond to the usual procedure employed by a surgeon. Preferably, the second image is obtained from a lateral direction, wherein before imaging, a computer-aided navigation system determines whether an imaging direction is parallel to the transcondylar plane.

Further, the femoral neck axis can be determined by means of the second image. Additionally, at least one of the first and second images can be acquired by using a stereotactic computer-aided surgery system. In particular, the computer-aided surgery system can use the images and information calculated and/or inputted by an operator to transform the corresponding data into a three-dimensional coordinate system. It can be advantageous to fix a tracking device or marker array to the femur or to a base on which the femur is placed.

A data carrier or storage device can be provided that comprises a program for realizing the methods described herein. Further, a program can be provided that, when executed on a computer or computer system realizes the steps according to the method described herein.

The method described herein comprises a procedure for measuring the antetorsion angle of the femur, such as the human femur. The antetorsion angle is defined as the angle between the femoral neck axis and the posterior condyle axis when projected onto a plane normal to the femoral shaft axis. The femoral neck axis is defined as the central axis through the femoral neck, and it runs through the center of the femoral head and is parallel to the cortical surface of the proximal part of the femoral neck. The posterior condyle axis connects the most posterior points of the femoral epicondyles. The femoral shaft axis is the central axis of the cylindrical shaft axis and is perpendicular to the posterior condyle axis. From these axes, it is possible to define a coordinate system in which the antetorsion angle can easily be measured by definition.

The transcondylar plane, which includes the posterior condyle axis and is parallel to the femoral shaft axis, is defined. The femoral shaft axis is defined by intersecting the plane tangential to the anterior cortex with a plane perpendicular to the posterior condyle axis. Once the femoral neck axis has been defined, it is possible to calculate the angle $\alpha$ between the femoral neck axis and the transcondylar plane. This angle $\alpha$ is then projected onto a plane perpendicular to the femoral shaft axis, in order to obtain the antetorsion angle $\gamma$. The posterior condyle axis and the femoral neck axis are each defined on a single fluoroscopic image, resulting in a total of two images for determining the antetorsion angle.

The system and method described herein are directed to defining an antetorsion angle $\gamma$ of a femur, such as a human femur. The antetorsion angle $\gamma$ can be defined by two angles $\alpha$ and $\beta$ which can be determined by means of two images of the femur, by taking the two images such that a coordinate system can be assembled, such that an equation can be used to calculate the antetorsion angle $\gamma$, wherein said equation reads as follows: $\tan \gamma = \tan \alpha'/\cos \beta$. If the second image is additionally tilted by an angle $\theta$ with respect to the normal of the transcondylar plane, then $\tan \gamma = \tan \alpha'/(\cos \beta \cdot \cos \theta)$.

BRIEF DESCRIPTION OF THE DRAWINGS

The forgoing and other features of the invention are hereinafter discussed with reference to the drawings.

DETAILED DESCRIPTION

Figure 1A:
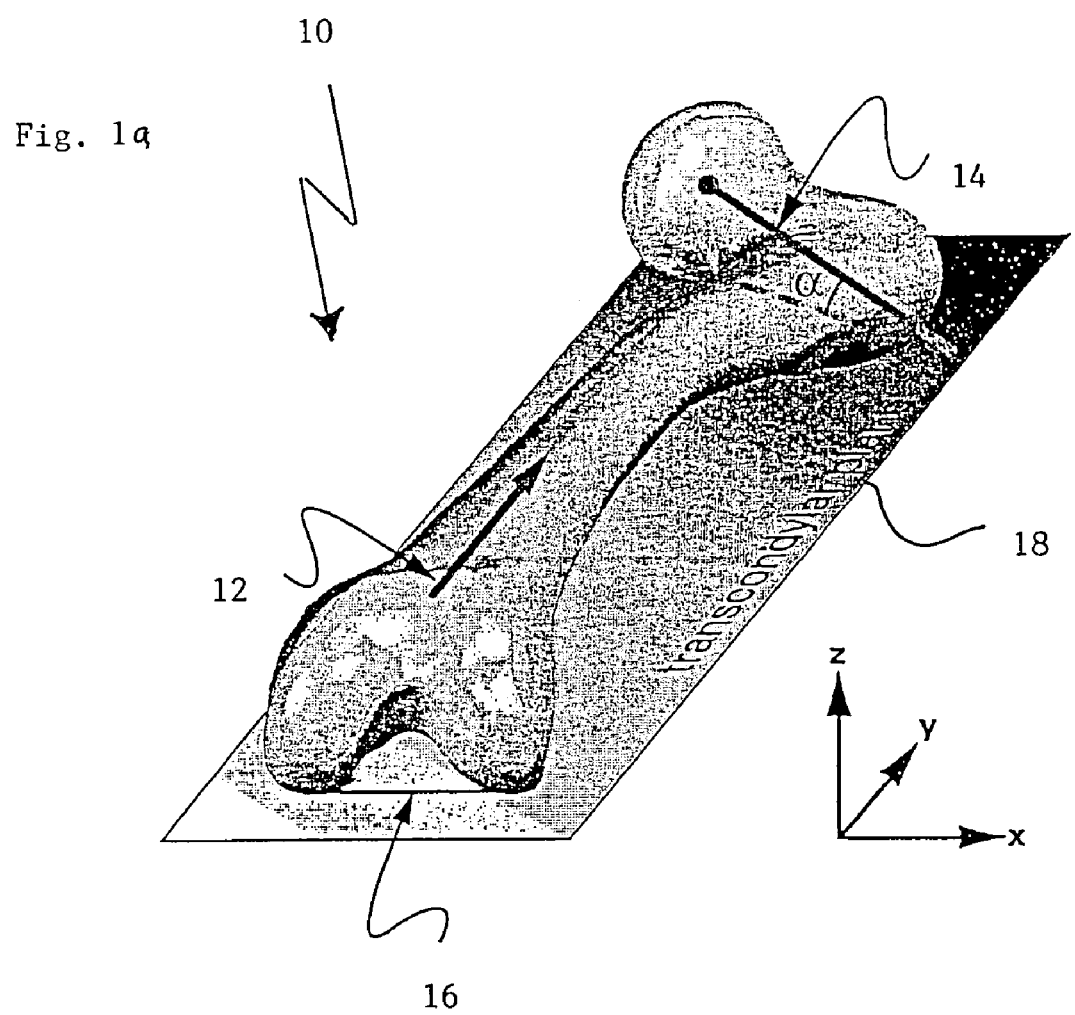
FIG. 1a shows an exemplary human femur and the orientation of the parts of the femur relative to an exemplary coordinate system.

FIG. 1a shows a human femur 10, wherein the femur has a particular orientation relative to an XYZ coordinate system. A transcondylar plane 18 is shown and is arranged parallel to the plane of the X and Y axes. A posterior condyle axis 16 is defined, as will be described below, and this posterior condyle axis 16 is a line within the transcondylar plane 18. A tangent 12 to the anterior cortex of the human femur 10 is parallel to the transcondylar plane 18. A femur neck axis 14 of the neck of the human femur 10 is elevated from the transcondylar plane 18, and the projection of the femoral neck axis 14 onto the transcondylar plane 18 encloses an angle $\alpha$.

Figure 1B:
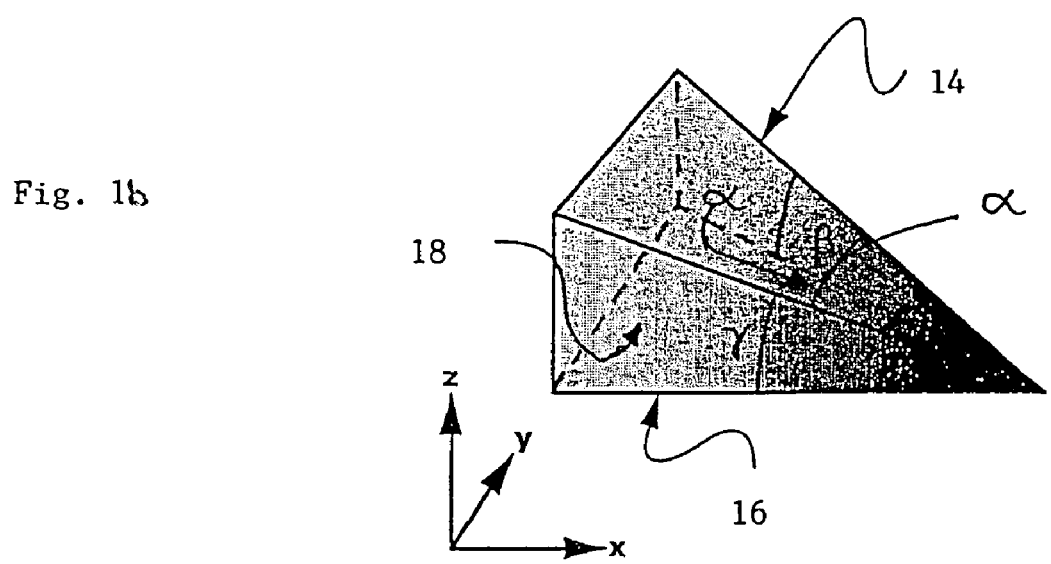
FIG. 1b shows an antetorsion angle $\gamma$ and a set of exemplary elements of the antetorsion angle.

The angles $\alpha$, $\beta$ and $\gamma$ are again shown in FIG. 1b, but in a more abstract form with respect only to the principal directions of the posterior condyle axis 16, the femoral neck axis 14 and the transcondylar plane 18, and with respect to the XYZ coordinate system. The angles are not shown with respect to the particular human femur represented by the geometrical elements 14, 16, 18.

Figure 1C:
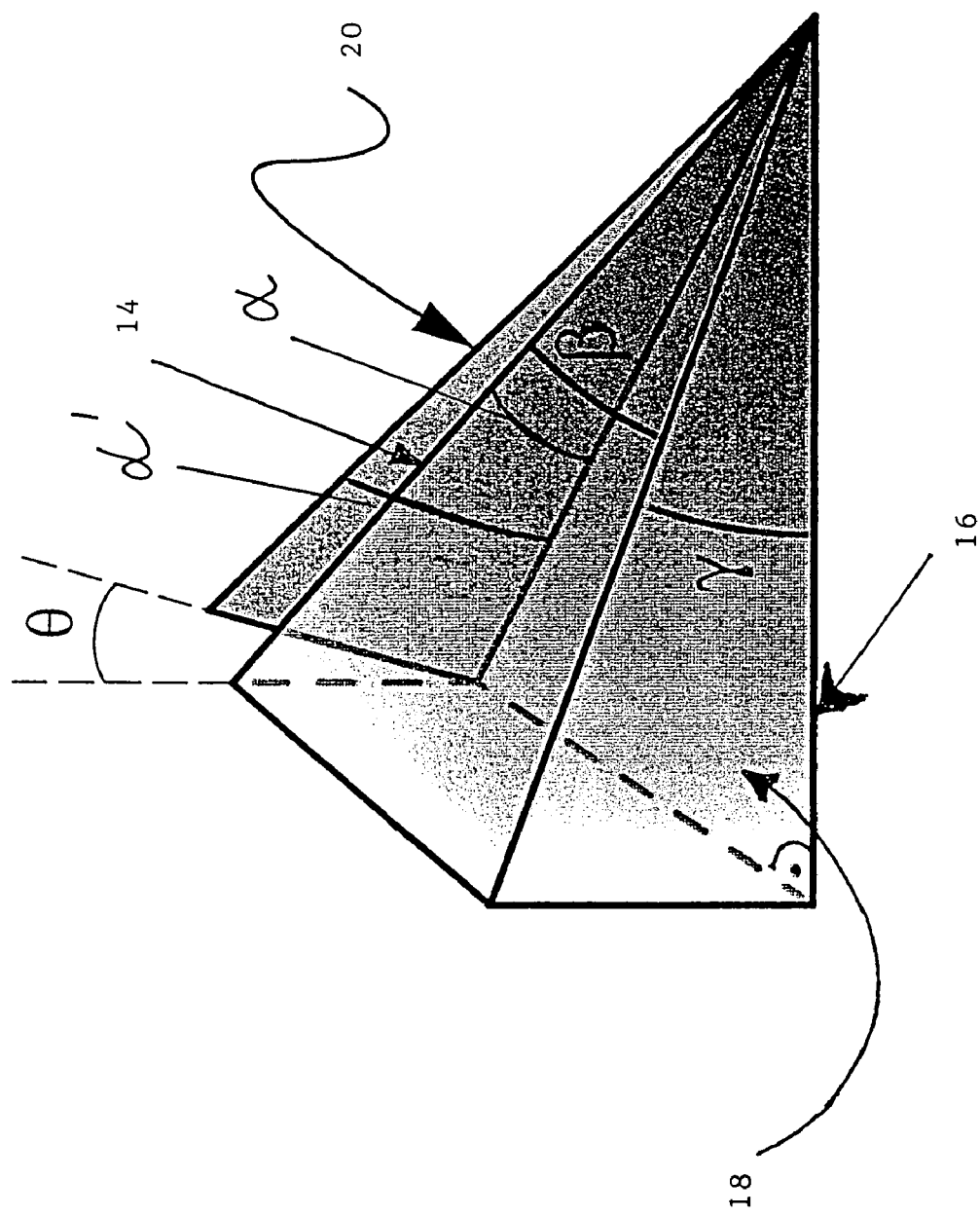
FIG. 1c shows the antetorsion angle $\gamma$ and another set of exemplary elements of the antetorsion angle.
Figure 1C:
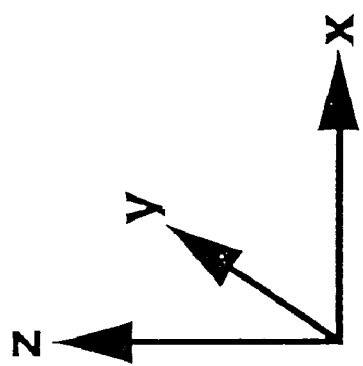

FIG. 1c shows another way of expressing the angles, wherein a difference with respect to FIG. 1b is that the second image of the femoral neck of the femur is not taken from a lateral direction. Instead, the second image is tilted with respect to the normal of the transcondylar plane. Accordingly, a plane 20 of the second image is tilted by an angle $\theta$ with respect to the normal of the transcondylar plane 18. This angle $\theta$ can be measured, for example, by measuring a tilt angle of the camera taking the second image. The tilt angle $\theta$ can be ensured relative to the orientation of the camera when taking the first image and thus with respect to the transcondylar plane 18. Due to this tilt angle $\theta$, the femoral neck axis encloses an angle $\alpha'$ with the transcondylar plane 18 which is different from the angle $\alpha$ according to FIG. 1c. If $\theta$ is close or equal to zero, $\alpha'$ is approximately or identically equal to $\alpha$. If $\theta$ occurs (e.g., $\theta$ is not zero), the equation for calculating $\gamma$ reads as follows: $\tan \gamma = \tan \alpha'/(\cos \beta \cdot \cos \theta)$.

Figure 2:
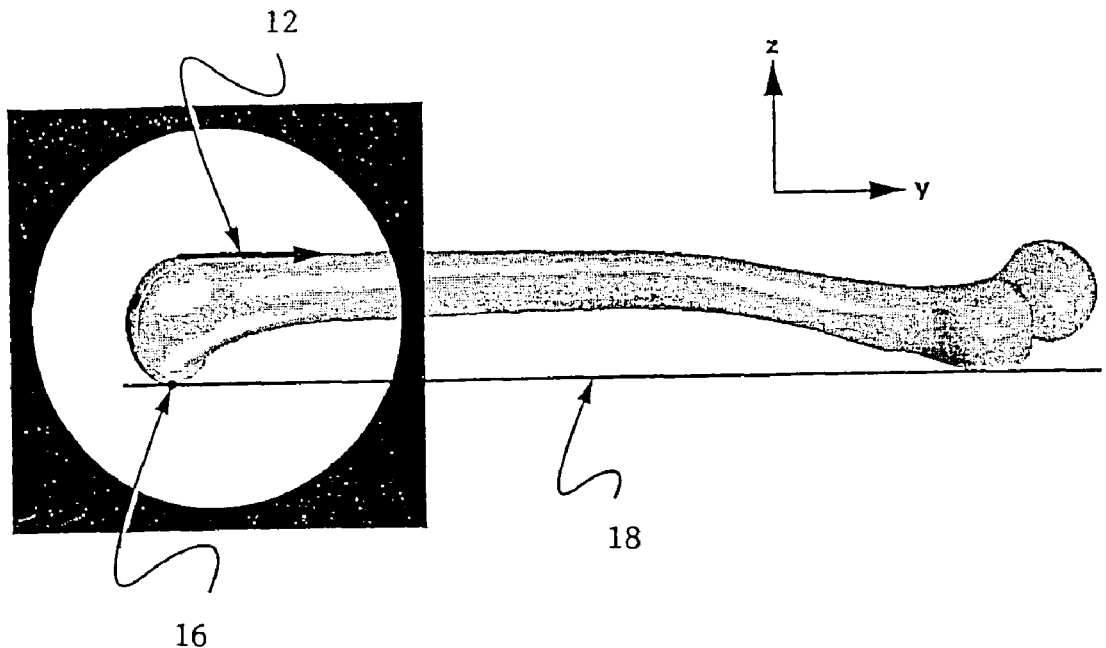
FIG. 2 is a lateral image of the exemplary femur.

FIG. 2 shows a lateral image of the distal femur. In this truly lateral image, the posterior condyles overlap. Therefore, the posterior condyle axis is a single point to be identified by the surgeon or by a particular software analysing the corresponding truly lateral fluoroscopic image, e.g. the second image. In addition, the surgeon can be responsible for defining a most anterior tangent 12 to the anterior cortex of the distal femur in the second image, although this can also be accomplished by an image-analysing computer program. In summary, FIG. 2 yields the transcondylar plane 18 which can be used for obtaining the second image in a truly lateral orientation.

Figure 3:
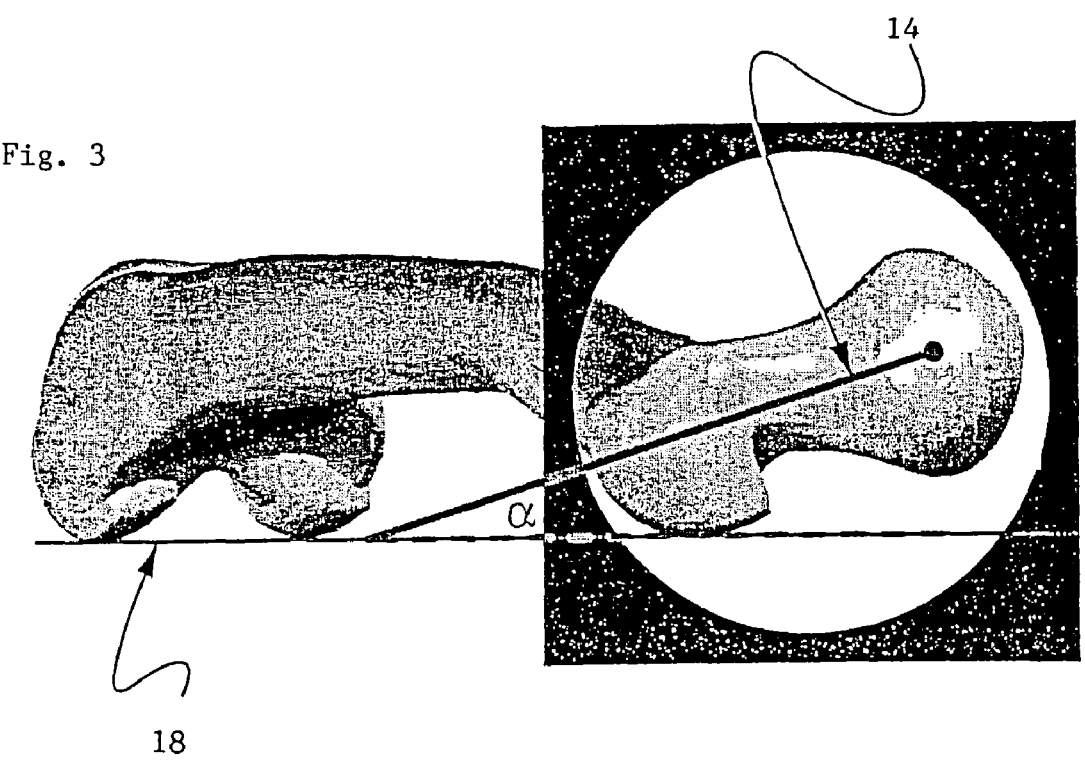
FIG. 3 an axial image of the femoral neck in combination with a corresponding perspective view of the remainder of the human femur.

In FIG. 3, the femoral neck has been recorded to provide a special axial image, wherein the normal of the image is parallel to the transcondylar plane 18. The image direction points from a truly lateral position towards the human femur and in particular towards the femoral neck. The surgeon also can be responsible for defining the femoral neck axis 14 in this image although this task can also be realized by a suitable image analysing software. The femoral neck axis 14 encloses an angle $\alpha$ with the transcondylar plane 18.

The method according to the invention can be achieved by firstly obtaining a lateral image or truly lateral image of the posterior condyles. Such a truly lateral image is shown in FIG. 2, in which the posterior condyle axis appears to be a single point 16. This means that the two posterior condyles overlap in the first fluoroscopic image, e.g., a lateral fluoroscopic image. The term "truly" in connection with the lateral image, e.g., the first image, means that the posterior condyle axis is projected onto the single point, as stated above, and the normal to the image plane in parallel to the posterior condyle axis 16. By identifying this single point in the fluoroscopic image, the surgeon can spatially determine the posterior condyle axis. This first image of the posterior condyles can be used to define the most anterior tangent 12 to the anterior cortex of the distal femur. The two-dimensional nature of the first image and the orientation of the first image perpendicular to the second image is helpful in using a first fluoroscopic image as a plane in the XYZ coordinate system, e.g., in three-dimensional space. The plane of the first image can be shifted parallel to the posterior direction until it includes the posterior condyle axis 16, in order to define the transcondylar plane 18.

The transcondylar plane 18 then can be intersected with a plane normal to the posterior condyle axis 16 to provide a parallel to the femur shaft axis (which is parallel to the Y axis of the XYZ coordinate system shown in the figures). The parallel is the normal of the projection plane onto which the femoral neck axis 14 and the posterior condyle axis 16 are projected. The second image then can be obtained of the femoral neck, in the orientation indicated in FIG. 3. The second image can be an axial image and is a common projection which is often used by trauma surgeons. This image can be taken from a lateral direction, such that the two images can be assembled to provide a three-dimensional system, e.g., an orientation in the XYZ coordinate system. It is preferable to acquire the second image by using a navigation system to help identify whether the imaging direction is parallel to the transcondylar plane 18. The normal to the image plane of the second image encloses the angle $\beta$ with the femoral shaft axis which is parallel to the Y axis of the XYZ coordinate system mentioned in the figures.

By means of the second image, the operator or surgeon can define the femoral neck axis which encloses the angle $\alpha$ with the transcondylar plane 18. It is then possible to use the coordinate system defined by the planes of the two images to calculate the antetorsion angle $\gamma$ by means of the equation $\tan \gamma = \tan \alpha/\cos \beta$ (when $\theta=0$, $\alpha=\alpha'$). If, the orientation of the second image is tilted with respect to the normal of the transcondylar plane 18 ($\tan \gamma = \tan \alpha'/\cos \theta$), the tilt angle $\theta$ has to be taken into account.

Figure 4:
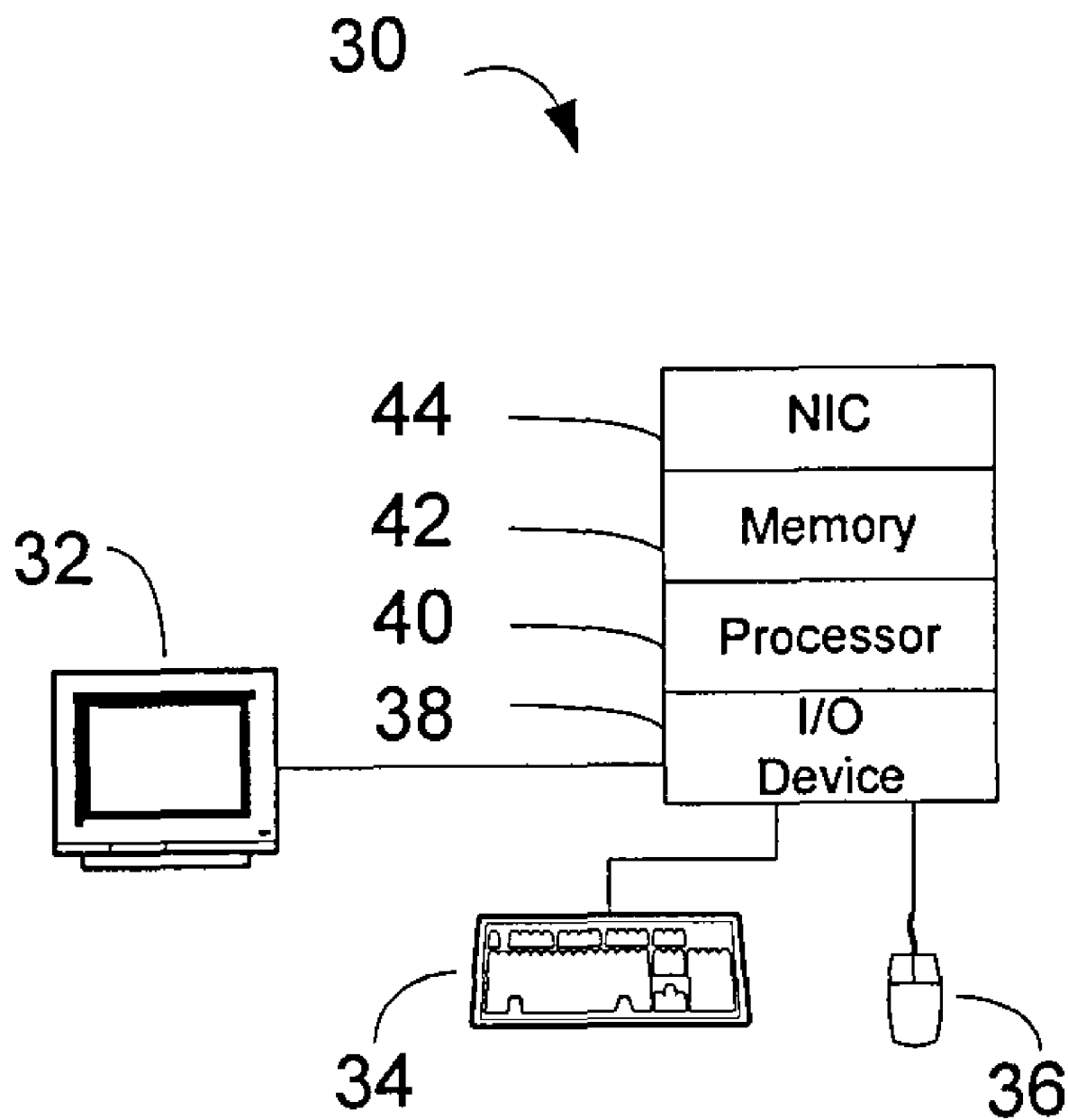
FIG. 4 is a block diagram of an exemplary computer system that can be used to carry out the method in accordance with invention.

FIG. 4 illustrates a computer system 30 that may be used to implement the method described herein. The computer system 30 may include a display 32 for viewing system information, and a keyboard 34 and pointing device 36 for data entry, screen navigation, etc. A computer mouse or other device that points to or otherwise identifies a location, action, etc., e.g., by a point and click method or some other method, are examples of a pointing device 36. Alternatively, a touch screen (not shown) may be used in place of the keyboard 34 and pointing device 36. The display 32, keyboard 34 and mouse 36 communicate with a processor via an input/output device 38, such as a video card and/or serial port (e.g., a USB port or the like).

A processor 40, such as an AMD Athlon 64® processor or an Intel Pentium IV® processor, combined with a memory 42 execute programs to perform various functions, such as data entry, numerical calculations, screen display, system setup, etc. The memory 42 may comprise several devices, including volatile and non-volatile memory components. Accordingly, the memory 42 may include, for example, random access memory (RAM), read-only memory (ROM), hard disks, floppy disks, optical disks (e.g., CDs and DVDs), tapes, flash devices and/or other memory components, plus associated drives, players and/or readers for the memory devices. The processor 40 and the memory 42 are coupled using a local interface (not shown). The local interface may be, for example, a data bus with accompanying control bus, a network, or other subsystem.

The memory may form part of a storage medium for storing information, such as application data, screen information, programs, etc., part of which may be in the form of a database. The storage medium may be a hard drive, for example, or any other storage means that can retain data, including other magnetic and/or optical storage devices. A network interface card (NIC) 44 allows the computer system 30 to communicate with other devices.

A person having ordinary skill in the art of computer programming and applications of programming for computer systems would be able in view of the description provided herein to program a computer system 30 to operate and to carry out the functions described herein. Accordingly, details as to the specific programming code have been omitted for the sake of brevity. Also, while software in the memory 42 or in some other memory of the computer and/or server may be used to allow the system to carry out the functions and features described herein in accordance with the preferred embodiment of the invention, such functions and features also could be carried out via dedicated hardware, firmware, software, or combinations thereof, without departing from the scope of the invention.

Computer program elements of the invention may be embodied in hardware and/or in software (including firmware, resident software, micro-code, etc.). The invention may take the form of a computer program product, which can be embodied by a computer-usable or computer-readable storage medium having computer-usable or computer-readable program instructions, "code" or a "computer program" embodied in the medium for use by or in connection with the instruction execution system. In the context of this document, a computer-usable or computer-readable medium may be any medium that can contain, store, communicate, propagate, or transport the program for use by or in connection with the instruction execution system, apparatus, or device. The computer-usable or computer-readable medium may be, for example but not limited to, an electronic, magnetic, optical, electromagnetic, infrared, or semiconductor system, apparatus, device, or propagation medium such as the Internet. Note that the computer-usable or computer-readable medium could even be paper or another suitable medium upon which the program is printed, as the program can be electronically captured, via, for instance, optical scanning of the paper or other medium, then compiled, interpreted, or otherwise processed in a suitable manner. The computer program product and any software and hardware described herein form the various means for carrying out the functions of the invention in the example embodiments.

Although the invention has been shown and described with respect to a certain preferred embodiment or embodiments, it is obvious that equivalent alterations and modifications will occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments of the invention. In addition, while a particular feature of the invention may have been described above with respect to only one or more of several illustrated embodiments, such feature may be combined with one or more other features of the other embodiments, as may be desired and advantageous for any given or particular application.

What is claimed is:

1. A method for determining an antetorsion angle of a femur, said antetorsion angle $\gamma$ being defined by an angle between
    a central axis through the femoral neck of said femur, said central axis running through the center of the femoral neck and being parallel to a cortical surface of a proximal part of the femoral neck, and
    a posterior condyle axis, said posterior condyle axis connecting the most posterior points of the femoral condyles of the femur if the central axis through the femoral neck and the posterior condyle axis are projected onto a plane normal to the femoral shaft axis, wherein the femoral shaft axis is the central axis of the approximately cylindrically shaped shaft of the femur, the central axis of the cylindrical shaft being parallel to the most anterior tangent to the distal femur, and the femoral shaft axis of said femur also being perpendicular to the posterior condyle axis;
    said method comprising:
    (a) obtaining via an imaging system a first image of the posterior condyles of the femur, such that the posterior condyles overlap laterally, wherein the posterior condyle axis is projected onto a point, and the normal to an image plane of the first image is parallel to the posterior condyle axis;
    (b) defining in the first image the most anterior tangent to the anterior cortex of the distal femur;
    (c) shifting said tangent parallel to itself until it includes the point of the posterior condyle axis in the first image, thereby determining a transcondylar plane;
    (d) determining a parallel to the femoral shaft axis in the first image;
    (e) obtaining via the imaging system a second image of the femoral neck of the femur such that the normal to an image plane of the second image encloses an angle $\beta$ with the femoral shaft axis and an angle $\theta$ with the transcondylar plane;
    (f) defining in the second image the femoral neck axis of the femur enclosing an angle $\alpha$ with the transcondylar plane;
    (g) calculating, using a processor, the antetorsion angle $\gamma$ from the equation $\tan \gamma = \tan \alpha'/(\cos \beta \cdot \cos \theta)$.

2. The method of claim 1, wherein obtaining the second image includes obtaining the second image from a lateral direction, such that $\cos \theta = 1$ or approaches 1, and wherein calculating the antetorsion angle $\gamma$ includes using the equation $\tan \gamma = \tan \alpha'/\cos \beta$ to calculate the antetorsion angle $\gamma$.

3. The method according to claim 2, wherein obtaining the second image includes prior to obtaining the second image using a computer-aided navigation system to determine whether an imaging direction is parallel to the transcondylar plane.

4. The method according to claim 1, wherein obtaining the first and/or second image includes obtaining at least one fluoroscopic image.

5. The method according to claim 4, wherein obtaining the second image includes obtaining the second image from a lateral direction, wherein prior to obtaining the second image a computer-aided navigation system is used to determine whether an imaging direction is parallel to the transcondylar plane.

6. The method according to claim 1, wherein obtaining the second image includes obtaining the second image from a lateral direction, wherein prior to obtaining the second image a computer-aided navigation system is used to determine whether an imaging direction is parallel to the transcondylar plane.

7. The method according to claim 1, wherein determining the parallel includes intersecting the transcondylar plane with a plane normal to the posterior condyle axis.

8. The method according to claim 7, wherein obtaining the second image includes obtaining the second image from a lateral direction, wherein prior to obtaining the second image a computer-aided navigation system is used to determine whether an imaging direction is parallel to the transcondylar plane.

9. The method according to claim 1, wherein obtaining the second image includes using an axial image of the femoral neck as the second image.

10. The method according to claim 1, wherein obtaining the first and/or second image includes using a stereotactic computer-aided surgery system to acquire at least one of the first and second images.

11. The method according to claim 1, further comprising transforming information calculated and/or input by an operator to project corresponding data into a three-dimensional coordinate system.

12. The method according to claim 1, further comprising attaching a tracking device to the femur or a base.

13. The method according to claim 12, wherein the base is an operation table on which the femur is placed.

14. A computer program embodied on a non-transitory computer readable medium for determining an antetorsion angle of a femur, said antetorsion angle $\gamma$ being defined by an angle between
   a central axis through a femoral neck of said femur, said central axis running through a center of the femoral neck and parallel to a cortical surface of a proximal part of the femoral neck, and
   a posterior condyle axis, said posterior condyle axis connecting the most posterior points of the femoral condyles of the femur when the central axis through the femoral neck and the posterior condyle axis are projected onto a plane normal to the femoral shaft axis, wherein the femoral shaft axis is the central axis of the approximately cylindrically shaped shaft of the femur, the central axis of the cylindrical shaft being parallel to the most anterior tangent to the distal femur, and the femoral shaft axis also being perpendicular to the posterior condyle axis;
said computer program comprising:
   (a) code that directs the capture of a first image of the posterior condyles of the femur such that the posterior condyles overlap laterally, wherein the posterior condyle axis is projected onto a point, and the normal to the image plane is parallel to the posterior condyle axis;
   (b) code that defines in the first image the most anterior tangent to the anterior cortex of the distal femur;
   (c) code that shifts said tangent parallel to itself until it includes the point of the posterior condyle axis in the first image, thereby determining a transcondylar plane;
   (d) code that determines a parallel to the femoral shaft axis in the first image;
   (e) code that directs the capture of a second image of the femoral neck of the femur such that the normal to the image plane of the second image encloses an angle $\beta$ with the femoral shaft axis and an angle $\theta$ with the transcondylar plane;
   (f) code that defines in the second image the femoral neck axis enclosing an angle $\alpha'$ with the transcondylar plane; and
   (g) code that calculates the antetorsion angle $\gamma$ via the equation $\tan \gamma = \tan \alpha'/(\cos \beta \cdot \cos \theta)$.

15. The program of claim 14, wherein the code that directs the capture of the second image includes code that directs the capture of the second image from a lateral direction, such that $\cos \theta = 1$ or approaches 1, and the antetorsion angle $\gamma$ is calculated from the equation $\tan \gamma = \tan \alpha'/\cos \beta$.

16. A system for determining an antetorsion angle of a femur, said antetorsion angle $\gamma$ being defined by an angle between
   a central axis through a femoral neck of said femur, said central axis running through a center of the femoral neck and parallel to a cortical surface of a proximal part of the femoral neck, and
   a posterior condyle axis, said posterior condyle axis connecting the most posterior points of the femoral condyles of the femur when the central axis through the femoral neck and the posterior condyle axis are projected onto a plane normal to the femoral shaft axis, wherein the femoral shaft axis is the central axis of the approximately cylindrically shaped shaft of the femur, the central axis of the cylindrical shaft being parallel to the most anterior tangent to the distal femur, and the femoral shaft axis also being perpendicular to the posterior condyle axis;
said system comprising:
   a processor and memory; and
   logic stored in memory and executable by the processor, said logic including:
   (a) logic that directs the capture of a first image of the posterior condyles of the femur such that the posterior condyles overlap laterally, wherein the posterior condyle axis is projected onto a point, and the normal to the image plane is parallel to the posterior condyle axis;
   (b) logic that defines in the first image the most anterior tangent to the anterior cortex of the distal femur;
   (c) logic that shifts said tangent parallel to itself until it includes the point of the posterior condyle axis in the first image, thereby determining a transcondylar plane;
   (d) logic that determines a parallel to the femoral shaft axis in the first image;
   (e) logic that directs the capture of a second image of the femoral neck of the femur such that the normal to the image plane of the second image encloses an angle $\beta$ with the femoral shaft axis and an angle $\theta$ with the transcondylar plane;
   (f) logic that defines in the second image the femoral neck axis enclosing an angle $\alpha'$ with the transcondylar plane; and
   (g) logic that calculates the antetorsion angle $\gamma$ via the equation $\tan \gamma = \tan \alpha'/(\cos \beta \cdot \cos \theta)$.

* * * * *

UNITED STATES PATENT AND TRADEMARK OFFICE
CERTIFICATE OF CORRECTION

| | | |
|---|---|---|
| PATENT NO. | : 7,925,324 B2 | Page 1 of 1 |
| APPLICATION NO. | : 11/560372 | |
| DATED | : April 12, 2011 | |
| INVENTOR(S) | : Christian Maier | |

It is certified that error appears in the above-identified patent and that said Letters Patent is hereby corrected as shown below:

On the Title page, item [56] Related Foreign Priority Data should be added:

European Patent Application No. 05 025 014.1 filed November 16, 2005.

Signed and Sealed this
Fourteenth Day of June, 2011

David J. Kappos
*Director of the United States Patent and Trademark Office*